United States Patent [19]

White

[11] 4,175,008

[45] Nov. 20, 1979

[54] CULTURE SPECIMEN COLLECTION AND TRANSPORT PACKAGE

[75] Inventor: Douglas J. White, Nutley, N.J.

[73] Assignee: Bio-Pharmaceutical Packaging Corp., Clifton, N.J.

[21] Appl. No.: 919,212

[22] Filed: Jun. 26, 1978

[51] Int. Cl.² .............................................. C12B 1/00
[52] U.S. Cl. ................................. 435/295; 128/759; 206/15.2; 206/15.3; 206/209; 206/459; 206/569; 206/570
[58] Field of Search ...................... 128/2 R, 2 W, 269; 195/103.5 M, 139; 206/15.1, 15.2, 209, 216, 229, 361, 438, 15.3, 569, 570

[56] References Cited

U.S. PATENT DOCUMENTS

| | | | |
|---|---|---|---|
| 3,093,242 | 6/1963 | Huyck et al. | 206/210 |
| 3,783,104 | 1/1974 | Henshilwood et al. | 195/139 X |
| 3,783,106 | 1/1974 | Henshilwood | 128/2 W X |
| 3,890,204 | 6/1975 | Avery | 206/361 X |
| 3,966,558 | 6/1976 | Calva-Pelliler | 195/139 |

FOREIGN PATENT DOCUMENTS

| | | | |
|---|---|---|---|
| 1937021 | 7/1969 | Fed. Rep. of Germany | 128/269 |
| 1000022 | 8/1965 | United Kingdom | 128/269 |

*Primary Examiner*—Stephen Marcus
*Attorney, Agent, or Firm*—Lerner, David, Littenberg & Samuel

[57] ABSTRACT

A culture specimen collection and transport package for collection of a specimen and for transport thereof to a test facility. The culture specimen collection and transport package comprises an elongated stem having a swab on one end, and first and second tubular members. The first tubular member is for sterilizingly housing the swab prior to collection of a specimen, while the second tubular member contains a culture medium therein for insertion of the swab thereinto after collection of the specimen for maintaining the specimen in a viable condition during transport to the test facility. A sealing cap member is slidably mounted on the elongated stem for sealingly closing the first tubular member when the swab is disposed in the first tubular member and for sealingly closing the second tubular member when the swab is disposed in the second tubular member. The sealing cap member is slidably movable to a first position to provide a relatively long effective distance between the swab and the cap member for specimen collection purposes and is slidably movable to a second position to provide a relatively short effective distance between the swab and the cap member when the swab is inserted into the second tubular member. In this way, the length of the second tubular member for sealingly housing the swab after a specimen has been collected may be substantially shorter than the relatively long effective distance between the swab and the cap member for specimen collecting purposes, thereby reducing the possibility of contamination of the transport package and/or lab personnel, as well as reducing the loss of the specimen on the side walls of the second tubular member.

10 Claims, 5 Drawing Figures

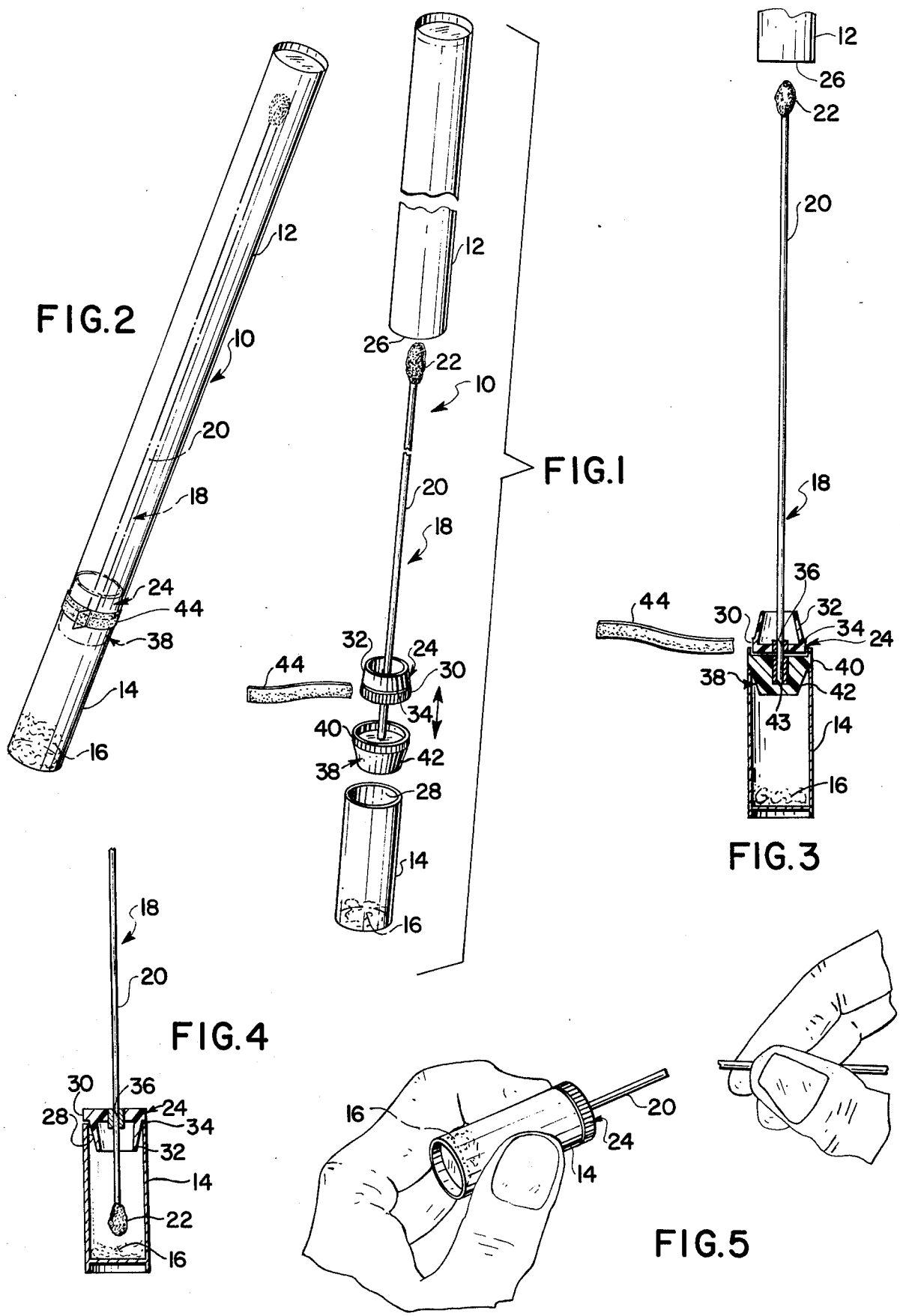

CULTURE SPECIMEN COLLECTION AND TRANSPORT PACKAGE

The present invention relates to culture specimen collection and transport packages, and more particularly to devices used by physicians and the like for collecting a specimen (referred to generally as a culture) from a selected area of the body and for maintaining the specimen in a viable condition, for example, during shipment to a test center for subsequent testing and identification. More particularly, the present invention is directed to such devices which are initially sterilized prior to collection of a specimen and which have a container in which the specimen is inserted and kept viable for a period of time after it has been collected by means of a sterile culture medium so that the specimen may be easily transported to a test facility. For example, such devices are particularly useful for collection of microorganisms, such as bacteria, from a patient's ears, nose, throat, and the like.

A variety of culture specimen collection and transport systems of this general type have been disclosed in the past. One such device is illustrated in U.S. Pat. No. 3,450,129 to Avery et al which discloses a device having a flexible outer tube within which is retained a frangible glass ampoule having a liquid culture sustaining medium sealed therein. Initially, the specimen collecting member, which comprises a swab on one end of an elongated handle, is sterilized and stored in the tube. The swab is then removed from the tube to collect a specimen and reinserted into the tube, and the tube is squeezed to break the ampoule and release the liquid. The liquid moistens an absorbant plug which is disposed within the tube in engagement with the tip of the swab so as to keep the swab moist until the culture is tested. In such devices, among other things, upon insertion of the swab into the tube after a specimen has been collected, the swab head must move along the entire length of the tube so that the cap on the end of the handle can seal the tube for shipment to the testing laboratory or facility. Such movement along the length of the tube can result in contamination of the transport package and/or cross contamination of lab personnel or other personnel collecting the specimen, as well as loss of the specimen on the side walls of the tube.

Another type of transport and collection package is illustrated in U.S. Pat. Nos. 3,783,104 to Henshilwood et al and 3,783,106 to Henshilwood. In the devices of these patents, there is disclosed a two compartment system in which the swab member is initially stored and sterilized prior to collection of a specimen in a first compartment and which, after a specimen is collected, is then inserted into a second tubular member containing the culturing medium for maintaining the specimen in a viable condition for transport to a testing facility. However, such devices still require that the swab head traverse the relatively long length of the tube containing the culturing medium after the specimen has been collected.

Further in this regard, it is to be noted that in the Henshilwood devices both have the sealing cap member fixably located on the handle of the swab member intermediate the two ends. While such an arrangement does provide an advantage over other devices in that the length of the tubular member which must be traversed after a specimen has been obtained is not as great as the entire length between the swab and the end of the handle, the cap member being intermediate the two ends will interfere with the collection of some specimens. In other words, the devices of the Henshilwood patents do not provide for relatively long effective lengths between the swab member and the cap member for specimen taking purposes. Thus, the devices of the Henshilwood patents are not useful in obtaining specimens from hard to reach areas of a patient's body, such as for example, the throat, rectum and/or vagina, since the cap secured intermediate of the collecting member interferes with such collection.

SUMMARY OF THE INVENTION

These and other disadvantages of the prior art are overcome with the present invention which discloses an improved culture specimen collection and transport package. The improved collection and transport package comprises an elongated stem having a specimen collecting member at one end thereof, a first tubular member for sterilizingly housing the specimen collecting member prior to the collection of a specimen and a second tubular member having a culture medium therein for insertion of the specimen collecting member thereinto after collection of a specimen for maintaining the specimen in a viable condition for transport to a testing facility. A cap member is slidably mounted on the elongated stem for sealingly closing the first tubular member when the specimen collecting member is disposed in the first tubular member and for sealingly closing the second tubular member when the specimen collecting member is disposed in the second tubular member. This cap member is movable between a first position and a second position, the first position providing a relatively long effective distance between the specimen collecting member and the cap member for specimen collecting purposes, and the second position providing a relatively short effective distance between the specimen collecting member and the cap member when the specimen collecting member is inserted into the second tubular member after collection of a specimen.

In this way, the length of the second tubular member for sealingly housing the specimen collecting member after a specimen has been collected is substantially shorter than the relatively long effective distance between the specimen collecting member and the cap for specimen collecting purposes. That is, the culture specimen collection and transport package of the present invention allows for a relatively short effective distance between such specimen collecting member and the cap after a specimen has been collected so that the specimen collecting member does not have to traverse a long distance into the tubular member having the culture medium therein. Thus, the slidable sealing cap member provides a convenient means for both shortening the distance that the specimen collecting member has to travel and for sealing the second tubular member. More importantly, in addition to this convenience, such an arrangement provides a safer method of handling by reducing the chances of contamination of the transport package (which might otherwise result during insertion of the specimen collecting member along a relatively long tubular length) and the consequent cross-contamination of lab personnel. Further still, the chances of a portion or all of the specimen being lost on the side walls of the tubular member is reduced. Yet, at the same time, the device of the present invention allows for relatively easy and efficient collection of a specimen by providing a relatively long effective distance between the specimen collecting member and the cap member.

In the preferred embodiment, the first tubular member is of a relatively long effective length and the cap member is in the first position when the specimen collecting member is sterilizingly housed in the first tubular member. In this way, the specimen collecting member and cap are initially arranged for specimen collection purposes so that the sterilized stem and specimen collecting member need not be handled excessively prior to collection of a specimen. After a specimen has been collected, the cap is simply slid along the elongated stem, the specimen collecting member inserted into the short second tubular member having a culturing medium therein, and the tubular member sealed with the cap member.

In a further preferred embodiment of the present invention, a second cap member is provided at the end of the elongated stem opposite from the specimen collecting member. This second cap member serves to affix the second tubular member to the elongated stem prior to collection of a specimen, as well as to initially seal the second tubular member. Thus, the second tubular member and the first tubular member may be arranged in coaxial, end to end relationship with the open ends of each adjacent to one another. This arrangement provides for relatively simple and convenient storage of the package prior to specimen collection.

These and further features and characteristics of the present invention will be apparent from the following detailed description in which reference is made to the enclosed drawings which illustrate the preferred embodiment of the present invention.

BRIEF DESCRIPTION OF THE DRAWINGS

FIG. 1 is a partially exploded perspective view of the improved culture specimen collection and transport package of the present invention, illustrating the various components;

FIG. 2 is a perspective view of the culture specimen collection and transport package of the present invention in its initial assembled arrangement prior to specimen collection;

FIG. 3 is a longitudinal cross-sectional view of the culture specimen collection and transport package of the present invention with the long tubular member removed, but still prior to collection of a specimen;

FIG. 4 is a longitudinal cross-sectional view, similar to FIG. 3, showing the specimen collection member inserted into the short tubular compartment after a specimen has been collected; and FIG. 5 is a perspective view of the short tubular member with the specimen member inserted and sealed therein after a specimen has been collected and showing the elongated stem being broken so that the short tubular member may be easily transported to a test facility.

DETAILED DESCRIPTION OF THE INVENTION

Referring now to the drwings in which like reference characters represent like elements, there is shown in FIG. 1 the component parts of the culture specimen collection and transport package 10 of the present invention. In general, the specimen collection and transport package is used by the medical profession for obtaining a specimen (customarily called a culture), for example of bacteria or other microorganisms, from a particular area of a patient's body, such as for example, the ears, nose, or throat, in order to determine if the patient is infected with certain types of organisms.

As shown in FIG. 1, the specimen collection transport package 10 is comprised of a relatively long tubular housing 12, a relatively short tubular housing 14 having a culturing medium 16 therein, and a specimen collection unit 18. The tubular housings 12, 14 are generally made of either glass or transparent plastic, although any suitable material may be utilized. The collection unit 18 in turn is comprised of an elongated stem or rod 20 having a specimen collecting member or element 22 at one end thereof and having a cap member or other closure means 24 arranged at the opposite end. As shown in FIG. 2, the major portion of the elongated stem 20 of the specimen collection unit 18 and the collecting member 22 are initially housed and maintained in a sterilized condition within the relatively long tubular housing 12 prior to collection of a specimen. The open end 26 of the tubular housing 12 is closed and sealed by cap member 24. When the collection and transport package 10 is to be used to collect a specimen, the cap member 24 is loosened and the collecting member 22 is simply withdrawn from the long tubular housing 12.

Generally, the specimen is collected on the specimen collecting member 22 by contacting the particular area of the patient's body with the member 22. For this purpose, it is expedient to have the collecting member 22 comprise a swab of absorbant material such as for example, cotton or calcium algnate, etc., wound around the end of the elongated stem 20. The stem 20 in turn may be made of any suitable material although it is generally made of wood or plastic. After the culture or specimen has been collected, it is necessary to place the specimen in a container to keep it in a dormant, yet viable state until it is subsequently tested. Generally, the swab 22 is placed in a container having a small amount of liquid or other kind of medium therein to moisten the swab 22 and maintain the specimen in a viable state during the interval between collection and subsequent testing. For this purpose, any standard culture sustaining medium may be utilized, as is well known in the art.

In the prior devices for specimen collection and transportation, it was necessary for the specimen collecting swab to traverse the length of a relatively long tubular housing so that the swab was placed in the location of the culturing medium, usually at the closed end of the long tubular housing. As can be appreciated, in traversing such a long length, part of the specimen can be lost on the side walls of the tubular container. In addition, this can result in the elongated stem also becoming contaminated with the specimen with the result of possible cross-contamination of lab personnel who eventually handle the transport package during testing. Thus, it is desirable that the specimen collecting swab be placed quickly and easily in contact with the culturing medium without having to traverse the long tubular length.

To accomplish this, in accordance with the present invention, the tubular member 14 containing the culturing medium 16 is of a relatively short length and the cap member 24 located at the opposite end of the stem 20 from the swab 22 is slidably mounted on the stem 20. As noted above, prior to collection of a specimen, the cap member 24 seals the stem 20 and swab member 22 within the relatively long tubular housing 12 to maintain the stem and collecting swab 22 in sterilized condition. When the swab 22 is removed for specimen collection purposes, a relatively long effective distance between the cap 24 and the swab 22 is provided, substantially corresponding to the length of the tubular housing 12, for ease in collecting a specimen or culture. This is especially useful for taking specimens in hard to reach body areas, such as for example may be the case with throat, rectal or vaginal specimens.

After collection of a specimen, the swab 22 is to be inserted into and sealed in the relatively short tubular housing 14 containing the culture medium 16, for eventual transportation to the testing facility. As seen in FIG. 4, the culture medium 16 is located at a relatively short distance from the open end 28 of the short tubular housing 14, due to the short length of the tubular housing 14. In practice, after a specimen has been collected, the cap member 24 is slid toward the swab member 22 to shorten the distance between the cap 24 and the swab 22 and the swab member 22 is then inserted into the short tubular housing 14. The cap 24 then closes and seals the open end 28 of the short tubular housing 14. Thus, the swab material containing the specimen or culture does not have to traverse a long length to be placed in the culture sustaining medium 16. Rather, only a relatively short distane need be traversed. Therefore, it is relatively easy to insert the swab 22 directly into contact with the culturing medum 16 without contacting the side walls of the housing 14. This in turn minimizes the possibility of contamination of the tubular member 14 and/or lab personnel during testing, as well as reducing the chance of loss of the specimen.

As shown in FIG. 4, after insertion of the swab 22 into the short tubular member 14, the stem 20 may be broken off beyond the cap member 24 and swab member 22 so that the specimen, sealed in the tubular housing 14, can be easily transported to the test facility. As can be appreciated, transportation and storage of the specimen or culture after it has been collected is much simpler with this arrangement than with prior art systems which required a relatively large complicated housing in which the entire specimen collection member and elongated handle, used for purposes of specimen collection had to be shipped to a testing facility.

The slidable cap member 24 is provided with a substantially cylindrical gripping section 30 and a tapered section 32. The tapered section 32 at the end adjacent the cylindrical gripping section 30 is of a slightly larger diameter than the inner diameter of the tubular housings 12, 14 and tapers to a diameter less than the inner diameter of the tubular housings 12, 14. This is advantageous for ease of insertion of the tapered section 32 into the open ends 26, 28 of the tubular housing 12, 14, and also for sealingly closing such open ends 26, 28. On the other hand, the cylindrical gripping section 30 is of a larger diameter than the inner diameters of the tubular members 12, 14 so that the cap member 24 may be easily gripped and removed from the tubular housings 12, 14. An annular lip 34 is provided between the cylindrical and tapered sections 30, 32, which serves as a stop for insertion of the cap member 24 into the tubular housings 12, 14. This annular lip 34 may also provide a seat for sealing of the open ends 26, 28 of the housings 12, 14. In addition, the cap member 24 includes an opening 36 therethrough for the elongated stem 20. Preferably, the opening 36 is sized to provide a relatively tight fit around the elongated stem 20 while also permitting the cap member 24 to slide therealong.

In the preferred embodiment, the specimen collection and transport package 10 is assembled so that the two tubular housings 12, 14 are arranged coaxially and in end to end relationship with the open ends 26, 28 of each adjacaent to one another. Further, the specimen collection unit 18 preferably includes a second cap member 38 similar to the slidable cap member 24 but which is fixably secured to the end of the elongated stem 20. The fixed cap member 38 serves to close and seal the short tubular housing 14 prior to collection of any specimen. The fixed cap member 38 is provided with a cylindrical gripping section 40 and a tapered section 42 of substantially the same size and shape as the cylindrical and tapered sections 30, 32, of the slidable cap member 24. However, the fixed cap member 38 differs from the slidable cap member 24 in that cap member 38 is substantially solid and includes a recessed opening 43 in which the end of the elongated stem 20 is locked.

It is preferred that the fixed cap member 38 is solid in order to provide a tight and complete seal to prevent entry of air into the tubular housing 14 prior to collection of any specimens which might contaminate or otherwise disturb the culture medium 16 contained therein. The reason why a tight and complete seal is desired, is that the specimen collection and transport package 10 of the present invention is designed to have a shelf life of approximately two years or longer. Therefore, it is necessary to maintain the culture medium 16 contained in the short tubular member 14 for a substantial period of time. On the other hand, after the specimen has been collected and the short tubular member is sealed by means of the slidable cap 24, the specimen should be tested in a relatively short period of time, say on the order of 24 hours. For such a relatively short period of time, the slidable cap member 24 does provide an adequate seal to maintain the viability of the specimen.

To assemble the culture specimen collection and transport package 10, the slidble cap member 24 is slid along the elongated stem 20 towards the fixed cap member 38 so that the two are arranged adjacent to one another. The two cap members 24, 38 are taped together by means of tape 44 around the cylindrical sections 30, 40 of each of the cap members 24, 28. This tape 44 serves to further seal against leakage of air which might otherwise contaminate the components of the package 10. Furthermore, by properly treating the tape 44, or by using appropriate material for the tape, the tape 44 could be used to provide an indication, such as for example by change of color, of whether the package 10 is sterilized or has remained sterilized over a period of time. Such tapes and materials which, for example, are sensitive to changes in heat, radiation, gas, moisture, etc., are known per se, but have not been employed in the field of the present invention.

As noted previously, the housing 12 serves to serilizingly house the specimen collecting member 22 prior to collection of a specimen. This can be accomplished by an conventional manner, such as for example, by sterilization of the individual components before assembly or even sterilization, such as by radiation or gas, after the components have been assembled into the overall package 10.

Further, it is to be noed that after use, the long tubular housing 12 in which the swab member 22 is initially sterilizingly housed, may be simply discarded, as are the fixed cap member 38 and portion of the stem 20 broken off.

Thus, in accordance with the present invention, it is apparent from the foregoing that the culture specimen and transport package 10 of the present invention provides a readily and easily usable specimen collecting member 22 located at the end of an elongated stem 20 to provide a relatively long effective specimen collection length to enable a physician or other user to easily collect a specimen, even in remote areas. In addition, by virtue of the slidable sealing cap member 24, the distance between the specimen collecting member 22 and the cap 24 may be shortened substantially to a length less than the desired length for specimen taking purposes, so that after a specimen has been collected, the collecting member 22 having the specimen thereon may be inserted directly into contact with the culture medium 16 in the short tubular housing 14 without having to contact the sides of the tubular member 14. This reduces the possibility of loss of some specimen along the side walls and/or contamination of the tubular member 14. Further, the elongated stem 20 may be broken off just above the cap 24 and collecting member 22 after the collecting member 22 has been secured and sealed within the tubular housing 14 for easy transport to a lab testing facility. In this way, it is ensured that the elongated stem 20 is not contaminated which might otherwise result in cross-contamination of lab personnel handling the transport package during testing of the specimen.

While the preferred embodiment of the present invention has been shown and described, it will be understood that such is merely illustrative and that changes may be made without departing from the scope of the invention as claimed.

What is claimed is:

1. A culture specimen and transport package comprising:
    an elongated stem having a first end and a second end;
    a specimen collecting member at said first end of said elongated stem;
    a first tubular member for sterilizingly housing said specimen collecting member prior to the collection of specimen;
    a second tubular member having a culture medium therein for insertion of said specimen collecting member thereinto after collection of a specimen for transport to a test facility;
    a first cap member slidably mounted on said elongated stem between said first and second ends for sealingly closing said first tubular member when said specimen collecting member is disposed in said first tubular member and for sealingly closing said second tubular member when said specimen collecting member is disposed in said second tubular member, said first cap member being movable between a first position and a second position, said first position providing a relatively long effective distance between said specimen collecting member and said first cap member for specimen collection purposes, and said second position providing a relatively short effective distance between said specimen collecting member and said first cap member when said specimen collecting member is inserted into said second tubular member after collection of said specimen; and
    a second cap member mounted at said second end of said elongated stem for affixing said second tubular member to said elongated stem prior to the collection of a specimen.

2. The culture specimen collection and transport package of claim 1 wherein the length of said first tubular member is greater than said relatively long effective distance and wherein said first cap member is in said first position when said specimen collecting member is sterilizingly housed in said first tubular member.

3. The culture specimen collection and transport package of claim 2 wherein said specimen collecting member comprises a swab of material wrapped around said first end of said elongated stem.

4. The culture specimen collection and transport package of claim 1 wherein said first position of said first cap member is adjacent said second cap member.

5. The culture specimen collection and transport package of claim 5 wherein said first and second tubular members include an open end and wherein prior to collection of specimen, said first and second tubular members are coaxially arranged with said open ends facing one another and said first and second cap members positioned therebetween.

6. The culture specimen collection and transport package of claim 5 including means for removably fixing said first cap member to said second cap member.

7. The culture specimen collection and transport package of claim 6 wherein said means for removably fixing said first cap member to said second cap member comprises a tape adhesively attachable to adjacent portions of said first and second cap members.

8. The culture specimen collection and transport package of claim 7 wherein said tape includes indicia for indicating a change in predetermined properties of the package.

9. The culture specimen collection and transport package of claim 5 wherein said first and second cap members include a tapered section, said tapered section of said first cap member facing said first end of said elongated stem and said tapered section of said second cap member facing away from said first end of said elongated stem, and said tapered sections tapering from a size greater than the size of said open ends of said first and second tubular members to a size less than the size of said open ends of said first and second tubular members.

10. The culture specimen collection and transport package of claim 1 wherein said first and second tubular members include an open end and wherein said first cap member includes a tapered section facing said first end of said elongated stem, said tapered section tapering from a size greater than the size of said open ends of said first and second tubular members to a size less than the size of said open ends of said first and second tubular members.

* * * * *